United States Patent
Kim et al.

(10) Patent No.: US 10,111,647 B2
(45) Date of Patent: Oct. 30, 2018

(54) APPARATUS AND METHOD FOR GENERATING ULTRASONIC IMAGE

(71) Applicant: SAMSUNG ELECTRONICS CO., LTD., Suwon-si (KR)

(72) Inventors: Bae Hyung Kim, Yongin-si (KR); Young-Il Kim, Suwon-si (KR); Jong-Keun Song, Yongin-si (KR); Seung-Heun Lee, Seoul (KR); Kyung-Il Cho, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1220 days.

(21) Appl. No.: 13/734,092

(22) Filed: Jan. 4, 2013

(65) Prior Publication Data

US 2013/0226000 A1    Aug. 29, 2013

(30) Foreign Application Priority Data

Jan. 4, 2012    (KR) .......................... 10-2012-0000810

(51) Int. Cl.
*A61B 8/00*    (2006.01)
*A61B 8/08*    (2006.01)
*G01S 7/52*    (2006.01)
*G01S 15/89*    (2006.01)

(52) U.S. Cl.
CPC .............. *A61B 8/483* (2013.01); *A61B 8/42* (2013.01); *A61B 8/54* (2013.01); *G01S 7/52047* (2013.01); *G01S 7/52092* (2013.01); *G01S 15/8952* (2013.01)

(58) Field of Classification Search
CPC ......... G01S 7/52092; A61B 8/52; A61B 8/54; A61B 8/483
See application file for complete search history.

(56) References Cited

U.S. PATENT DOCUMENTS

| | | | | |
|---|---|---|---|---|
| 5,358,466 A | * | 10/1994 | Aida | A61B 17/2256 600/439 |
| 6,168,565 B1 | | 1/2001 | Napolitano | |
| 6,231,511 B1 | * | 5/2001 | Bae | G01S 7/52046 600/447 |
| 6,514,205 B1 | * | 2/2003 | Lee | G01S 7/52026 367/138 |

(Continued)

FOREIGN PATENT DOCUMENTS

| KR | 2002-0079140 A | 10/2002 |
|---|---|---|
| KR | 10-2009-0009258 A | 1/2009 |

(Continued)

*Primary Examiner* — Joseph M Santos Rodriguez
(74) *Attorney, Agent, or Firm* — Sughrue Mion, PLLC (57) ABSTRACT

Provided is an ultrasonic image generating apparatus that may generate an ultrasonic image by using an ultrasonic transducer which has a wideband frequency transfer characteristic or an ultra-wideband frequency transfer characteristic, such as a micromachined ultrasonic transducer (MUT). A pulse generator of the ultrasonic image generating apparatus may generate a first ultrasonic pulse having a first center frequency and a first bandwidth and a second ultrasonic pulse having a second center frequency and a second bandwidth. The ultrasonic transducer may simultaneously transmit the first ultrasonic pulse and the second ultrasonic pulse.

11 Claims, 6 Drawing Sheets

(56) References Cited

U.S. PATENT DOCUMENTS

| | | | |
|---|---|---|---|
| 2004/0039282 A1* | 2/2004 | Szabo | G01S 7/52038 600/437 |
| 2005/0007882 A1* | 1/2005 | Bachelor | G01S 15/89 367/103 |
| 2007/0016020 A1 | 1/2007 | Oshiki et al. | |
| 2007/0038082 A1* | 2/2007 | Mo | B06B 1/064 600/437 |
| 2009/0076392 A1 | 3/2009 | Oshiki et al. | |
| 2009/0118619 A1 | 5/2009 | Oshiki | |
| 2009/0182235 A1 | 7/2009 | Robert et al. | |
| 2009/0234230 A1 | 9/2009 | Bercoff et al. | |
| 2009/0299182 A1 | 12/2009 | Asafusa | |
| 2009/0306512 A1* | 12/2009 | Loftman | G01S 7/52046 600/447 |

FOREIGN PATENT DOCUMENTS

| | | |
|---|---|---|
| KR | 10-2010-0068824 A | 6/2010 |
| KR | 10-2011-0058723 A | 6/2011 |

\* cited by examiner

APPARATUS AND METHOD FOR GENERATING ULTRASONIC IMAGE

CROSS-REFERENCE TO RELATED APPLICATION(S)

This application claims priority under 35 U.S.C. § 119(a) from Korean Patent Application No. 10-2012-0000810, filed on Jan. 4, 2012, in the Korean Intellectual Property Office, the entire disclosure of which is incorporated herein by reference for all purposes.

BACKGROUND

1. Field

The following description relates to an apparatus and method for generating an ultrasonic image, and more particularly, to an ultrasonic image generating apparatus which enhances a frame rate and a resolution of an ultrasonic image used for medical purposes, and an operation method thereof.

2. Description of Related Art

Using a noninvasive method, a medical ultrasonic imaging apparatus may provide anatomical and functional information relating to an interior portion of a human body in real time without causing any harm to the body. Therefore, the market related to the medial ultrasonic imaging apparatus is gradually growing.

A conventional ultrasonic medical imaging apparatus may provide information relating to a cross-section of an interior portion of a human body as a two-dimensional (2D) image by using a one-dimensional (1D) array transducer. A three-dimensional (3D) image may be obtained by acquiring volume information relating to the interior portion of the body while mechanically moving the 1D array transducer.

However, the above method for obtaining a 3D image based on the mechanical movement of the 1D array transducer may have a constrained performance in aspects of a temporal resolution or a spatial resolution relating to a corresponding image forming rate. Accordingly, there is an increasing interest regarding technology which is capable of acquiring a 3D image by using a 2D array transducer.

In order to practically apply advantages of a 3D image which is acquired by using a 2D array transducer, a frame rate and a resolution of an image may need to be simultaneously enhanced. A conventional system may have some deficiencies in relation to enhancing both factors.

SUMMARY

In one general aspect, there is provided a system which includes an apparatus for generating an ultrasonic image, including an ultrasonic transducer which has one of a wideband frequency transfer characteristic and an ultra-wideband frequency transfer characteristic, and a pulse generator which generates a plurality of ultrasonic pulses, wherein each pulse of the plurality of ultrasonic pulses has a different respective center frequency within a frequency band of the ultrasonic transducer.

In the wideband frequency transfer characteristic, a −6 dB bandwidth may be greater than 100% and less than 120% of a center frequency of the frequency band of the ultrasonic transducer, and in the ultra-wideband frequency transfer characteristic, a −6 dB bandwidth may be greater than 120% of the center frequency of the frequency band of the ultrasonic transducer.

The ultrasonic transducer may be configured by using one of a capacitive micromachined ultrasonic transducer (cMUT) and a piezoelectric micromachined ultrasonic transducer (pMUT).

The ultrasonic image generating apparatus may further include a controller which controls the pulse generator to receive a user selection which relates to at least one of a center frequency and a bandwidth of at least a respective one of the plurality of ultrasonic pulses via a user interface, such as, for example, a keyboard, a touch pad, and/or the like, or via a frequency selection interface, such as, for example, a button, a switch, an equalizer, and/or the like, and to aenerate an ultrasonic pulse which corresponds to the selected at least one of the center frequency and the bandwidth.

When the controller receives an instruction which relates to increasing a lateral resolution of the ultrasonic image to be generated, the controller may control the ultrasonic transducer to increase a number of ultrasonic focal points relating to the ultrasonic image to be generated.

Respective ultrasonic pulses which correspond to the ultrasonic focal points may be generated to be mutually orthogonal to each other, and the ultrasonic image generating apparatus may separate a received ultrasonic pulse by using the orthogonality of the respective ultrasonic pulses.

When the controller receives an instruction which relates to increasing an axial resolution of the ultrasonic image to be generated, the controller may control the ultrasonic transducer to decrease a number of ultrasonic focal points relating to the ultrasonic image to be generated.

Respective ultrasonic pulses which correspond to the ultrasonic focal points may include frequency divided signals that are generated to be mutually orthogonal to each other, and each of the respective ultrasonic pulses may be adjusted to have a maximum bandwidth within the frequency band of the ultrasonic transducer.

Sample signals received via the ultrasonic transducer may be wirelessly transmitted to an outside.

In another general aspect, there is provided an apparatus for generating an ultrasonic image, the apparatus including a pulse generator which generates a first ultrasonic pulse which has a first center frequency and a first bandwidth and a second ultrasonic pulse which has a second center frequency and a second bandwidth, and a transducer which simultaneously transmits the first ultrasonic pulse and the second ultrasonic pulse.

When the transducer receives a first reflected signal which relates to the first ultrasonic pulse and a second reflected signal which relates to the second ultrasonic pulse, storage may be performed by performing radio frequency (RF)-echo signal sampling with respect to each of the first reflected signal and the second reflected signal, and dynamic focusing is performed with respect to each of the first reflected signal and the second reflected signal.

By using at least one of a dynamic band pass filter and a dynamic low pass filter, a dynamic focused signal which results from the dynamic focusing may be separated into a first separated reflection signal having the first center frequency and the first bandwidth, and a second separated reflection signal having the second center frequency and the second bandwidth.

The dynamic band pass filter may be configured by using at least one of a matched filter, a correlator, an inverse filter, and a signal processor for separating respective frequency components of a received signal.

Each of the first separated reflection signal and the second separated reflection signal may be stored in association with a corresponding focal position, and an ultrasonic image of a target field of view may be generated by using the stored signals.

The target field of view may be received from a user via a user interface, and at least one of the first center frequency, the first bandwidth, the second center frequency, and the second bandwidth may be adjusted based on the target field of view.

When the transducer receives at least one of the first reflected signal and the second reflected signal, a corresponding focal position of the at least one received signal may be adjusted based on the target field of view.

In still another general aspect, there is provided an apparatus for generating an ultrasonic image, including a transducer which has one of a wideband frequency transfer characteristic and an ultra-wideband frequency transfer characteristic and which transmits a first ultrasonic pulse and a second ultrasonic pulse which respectively correspond to a target field of view set by a user, and which receives a reflected signal relating to at least one focal position which corresponds to the target field of view. An ultrasonic image which corresponds to the target field of view may be generated by separating the received reflected signal into a first separated reflection signal which corresponds to the first ultrasonic pulse and a second separated reflection signal which corresponds to the second ultrasonic pulse.

In yet another general aspect, there is provided a method for generating an ultrasonic image, the method including generating a first ultrasonic pulse which has a first center frequency and a first bandwidth and a second ultrasonic pulse which has a second center frequency and a second bandwidth, transmitting the first ultrasonic pulse and the second ultrasonic pulse by using an ultrasonic transducer which has an ultra-wideband transfer characteristic, and receiving a first reflected signal which corresponds to the first ultrasonic pulse and a second reflected signal which corresponds to the second ultrasonic pulse and using each of the first reflected signal and the second reflected signal to generate the ultrasonic image.

The ultrasonic image generating method may further include controlling the ultrasonic transducer to increase a number of ultrasonic focal points when an instruction which relates to increasing a lateral resolution of the ultrasonic image to be generated is received.

The ultrasonic image generating method may further include controlling the ultrasonic transducer to decrease a number of ultrasonic focal points when an instruction which relates to increasing an axial resolution of the ultrasonic image to be generated is received.

In a further another general aspect, there is provided a method for generating an ultrasonic image by using an ultrasonic image generating apparatus, the method including displaying a primary medical image by wirelessly transmitting before-beam focusing signals, displaying a secondary medical image by wirelessly transmitting after-beam focusing before-post processed signals, and displaying a tertiary medical image by wirelessly transmitting after-beam focusing post processed signals.

Other features and aspects will be apparent from the following detailed description, the drawings, and the claims.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, description of well-known functions and constructions may be omitted for increased clarity and conciseness.

Figure 1:
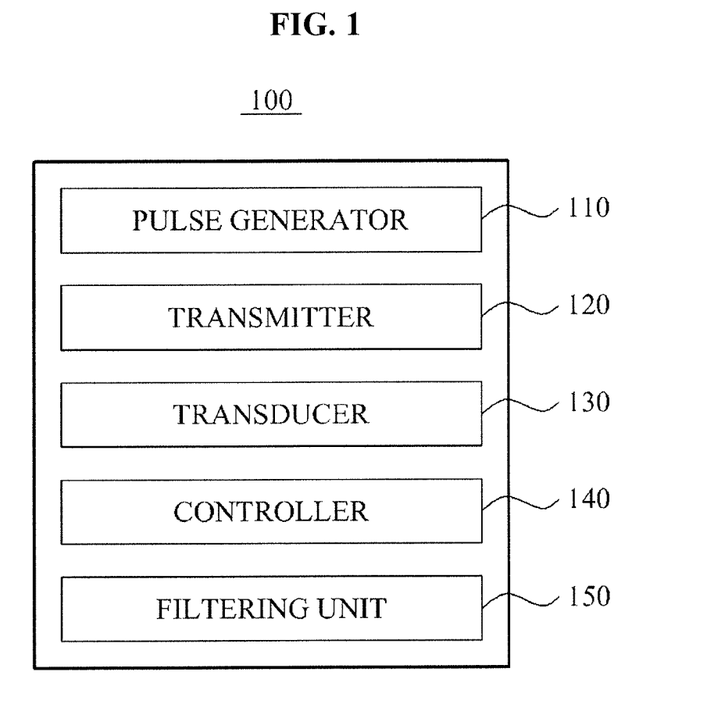
FIG. 1 is a block diagram which illustrates an example of an ultrasonic image generating apparatus, according to an exemplary embodiment.

FIG. 1 illustrates an example of an ultrasonic image generating apparatus 100, according to an exemplary embodiment.

In the related art, a center frequency component and a bandwidth of an ultrasonic transducer may be constrained, and it may be impossible to selectively adjust an ultrasonic signal of a single transducer to be suitable for purposes or characteristics of a particular diagnostic target. Accordingly, a single transducer may be selected for use from among a plurality of transducers having different center frequencies or different bandwidths based on the particular diagnostic target.

Further, due to constraints on a center frequency and/or constraints on a frequency band, the related art has a tradeoff relationship. Therefore, in the related art, when a resolution increases, a frame rate generally decreases, and when the frame rate increases, the resolution generally decreases.

Also, in the related art, due to one way dynamic focusing, degradation of a resolution may increase with a corresponding increase in distance from a focusing area.

According to exemplary embodiments, by using an array transducer which has one of a wideband frequency response characteristic and an ultra-wideband frequency response characteristic, it is possible to generate an ultrasonic image which is suitable for user purposes and/or suitable with respect to relevant characteristics of a diagnostic target.

For example, in the related art, a doctor who is a user may selectively use one of different transducers based on a portion of a human body to be diagnosed or a target disease to be diagnosed. However, according to exemplary embodiments, a single transducer may perform operations by using a wide or ultra-wide bandwidth transducer, such as, for example, a capacitive micromachined ultrasonic transducer (cMUT) or a piezoelectric micromachined ultrasonic transducer (pMUT). In an exemplary embodiment, a cMUT may have a −6 dB bandwidth which is greater than 120% of the center frequency, such as, for example, a −6 dB bandwidth which has a value within a range of between 120% and 180% of the center frequency. For example, a CMUT according to an exemplary embodiment may have a center frequency of 6.96 MHz and a −6 dB bandwidth of 11.62 MHz, which is approximately equal to 167% of the 6.96 MHz center frequency.

According to exemplary embodiments, a single transducer may replace various types of transducers and thus, it is possible to simplify a transducer lineup, to enhance a workflow of a medical process, and to decrease a diagnosis time.

Referring to FIG. 1, an ultrasonic image generating apparatus 100 according to an exemplary embodiment includes a pulse generator 110 which generates a plurality of ultrasonic pulses, each of which pulses has a different center frequency.

A transmitter 120 may transfer each of the plurality of ultrasonic pulses to a transducer 130 prior to converting each of the plurality of ultrasonic pulses to a corresponding ultrasonic signal. The transducer 130 may actually generate an ultrasonic signal and transmit the ultrasonic signal to a diagnostic target.

In this exemplary embodiment, the transducer 130 may have a wideband frequency transfer characteristic or an ultra-wideband frequency transfer characteristic.

A controller 140 may control the pulse generator 110 to receive a user selection which relates to at least one of a center frequency and a bandwidth of at least one of the plurality of ultrasonic pulses via a user interface (not shown), and to generate an ultrasonic pulse which corresponds to the selected center frequency and/or bandwidth.

Generated ultrasonic pulses may include a first ultrasonic pulse which has a first center frequency and a first bandwidth, a second ultrasonic pulse which has a second center frequency and a second bandwidth, and the like.

When a plurality of ultrasonic pulses having different respective center frequencies and suitable respective frequency bandwidths which are respectively based on user designated parameters is generated, the plurality of ultrasonic pulses may be simultaneously transmitted to the diagnostic target via the transducer 130.

When the controller 140 receives an instruction which relates to increasing a lateral resolution of an ultrasonic image to be generated, the controller 140 may control the transducer 130 to increase the number of ultrasonic focal points with respect to the ultrasonic image to be generated.

Respective ultrasonic pulses which correspond to the ultrasonic focal points may be generated to be mutually orthogonal to each other. After receiving reflected waves, the ultrasonic image generating apparatus 100 may separate the received reflected waves to correspond to respective corresponding frequency bands by using the orthogonality of the ultrasonic pulses.

When the controller 140 receives an instruction which relates to increasing an axial resolution of an ultrasonic image to be generated, the controller 140 may control the transducer 130 to decrease the number of ultrasonic focal points with respect to the ultrasonic image to be generated.

In this example, respective ultrasonic pulses which correspond to the ultrasonic focal points may include frequency divided signals that are generated to be mutually orthogonal to each other. Each of the ultrasonic pulses may be adjusted to have a maximum bandwidth within a frequency band of the transducer 130.

Figure 5:
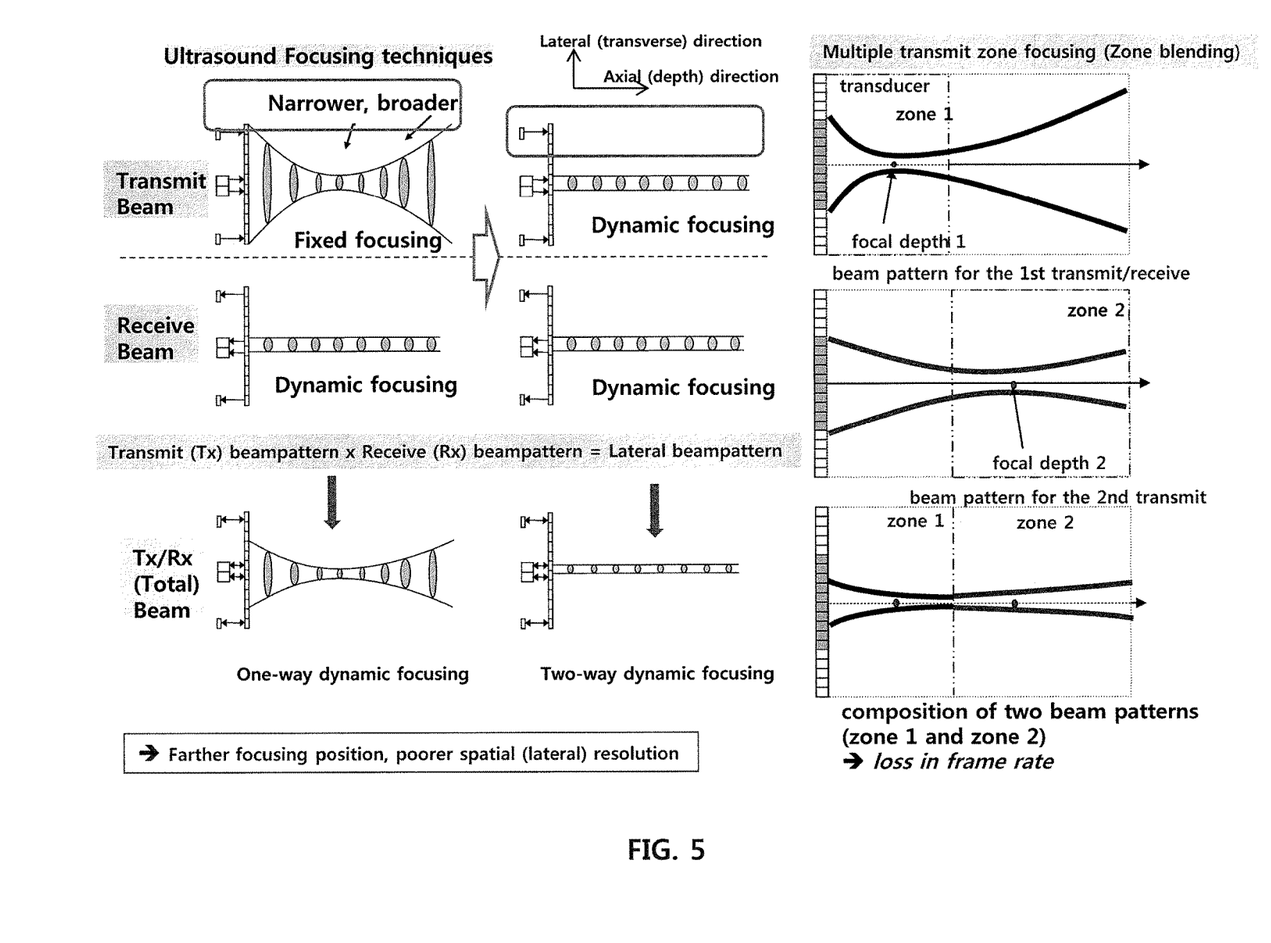
FIG. 5 is a diagram which illustrates ultrasound focusing techniques, according to an exemplary embodiment.

When the transducer 130 receives a first reflected signal which relates to the first ultrasonic pulse and a second reflected signal which relates to the second ultrasonic pulse, the ultrasonic image generating apparatus 100 may store a signal by performing radio frequency (RF)-echo signal sampling and may also perform dynamic focusing with respect to the first and second reflected signals, which dynamic focusing may result in a dynamic focused signal. For example, referring to FIG. 5, the transducer 130 may perform multiple transmit zone focusing, or zone blending, by which a transmit beam has a first zone and a second zone, and each of the first and second zones has a respective focal depth, and dynamic focusing is performed in order to obtain a dynamic focused signal.

The ultrasonic image generating apparatus 100 may further include a filter 150.

The filter 150 may be configured as, for example, a dynamic band pass filter or a dynamic low pass filter, and may separate the dynamic focused signal into a first separated reflection signal which has the first center frequency and the first bandwidth, a second separated reflection signal which has the second center frequency and the second bandwidth, and the like.

Figure 6:
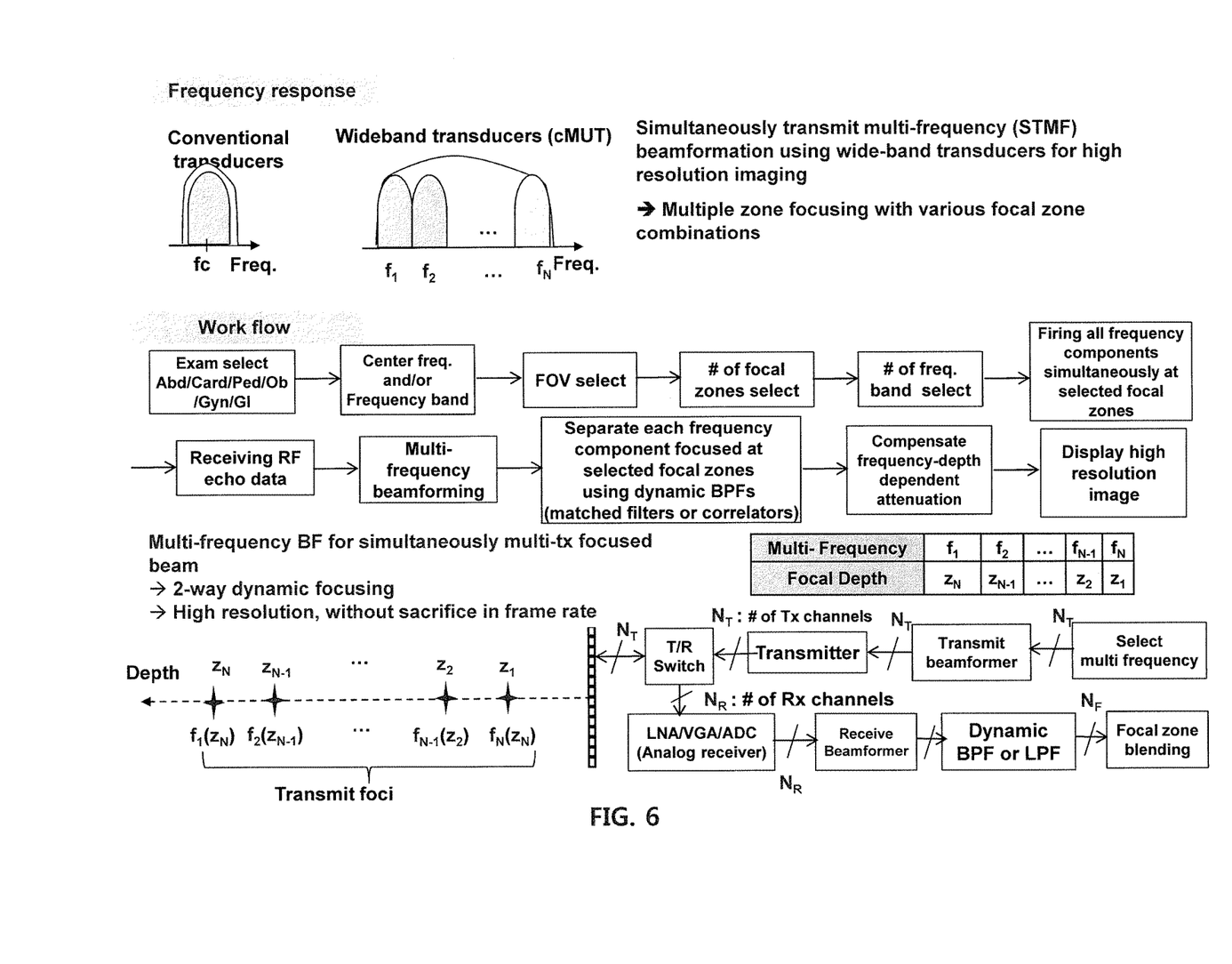
FIG. 6 is a diagram which illustrates a process for separating wideband and/or ultra-wideband signals into mutually orthogonal signals by using dynamic band pass filters, according to an exemplary embodiment.

Referring also to FIG. 6, the dynamic band pass filter may be configured by a signal processor or a filter to separate respective frequency components of a received signal. The dynamic band pass filter may include, for example, at least one of a demodulator, a matched filter, a correlator, an inverse filter, and the like.

A detailed operation of the apparatus 100 according to an exemplary embodiment will be described below with reference to FIG. 2.

Figure 2:
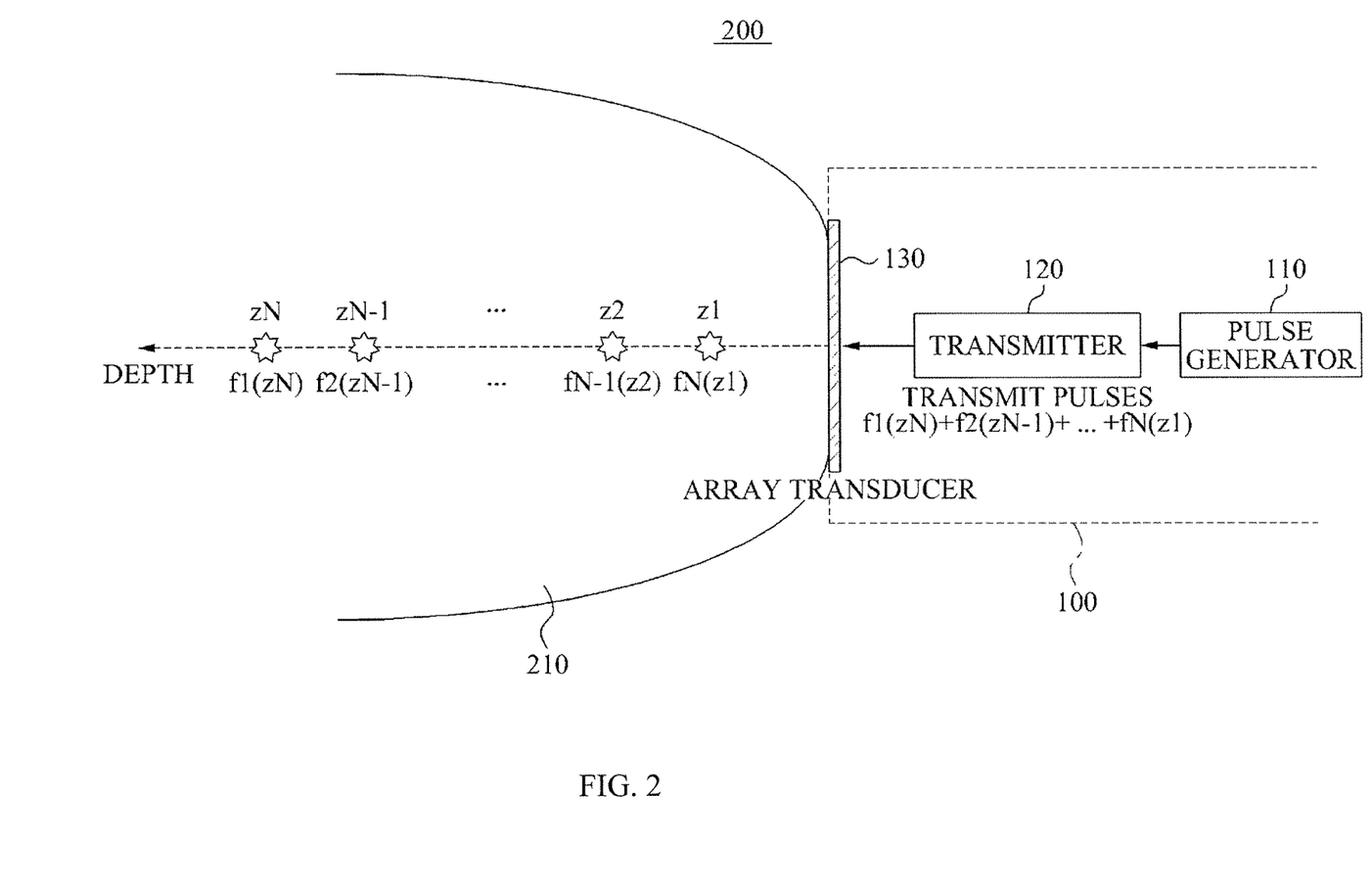
FIG. 2 is a diagram which illustrates an example in which an ultrasonic image generating apparatus transmits ultrasonic signals having different center frequencies and frequency bands, according to an exemplary embodiment.

FIG. 2 shows a diagram 200 which illustrates an example in which the ultrasonic image generating apparatus 100 transmits ultrasonic signals having different respective center frequencies and different respective frequency bands, according to an exemplary embodiment.

The ultrasonic image generating apparatus 100 may receive a user selection which relates to a field of view (FoV) that includes information relating to at least one of a width, a height, and the like of an ultrasonic image to be generated.

Various parameters may be manifested in the field of view. Various setting values which are used to determine a diagnostic area which is used in an ultrasonic image diagnostic device may be included in the parameters.

The transducer 130 may include an array transducer. The transducer 130 may have one of a wideband frequency transfer characteristic and an ultra-wideband frequency transfer characteristic. The transducer 130 may transmit a first ultrasonic pulse and a second ultrasonic pulse based on a target field of view set by a user, and may receive a reflected signal which relates to at least one focal position based on the target field of view and which relates to a medium 210 which is an object of the ultrasonic pulses, which falls within the target field of view. The medium 210 may include, for example, a tissue of a human body, a tissue of an animal body, and/or any other material relating to a bodily organ upon which evaluation or testing is to be performed.

The pulse generation may relate to a generation process for a pulse that is transferred by the pulse generator 110 and the transmitter 120 to the transducer 130 based on a control of the controller 140. However, even though further detailed description is not provided herein, except for a description which relates to a difference which is based on using an ultra-wideband transfer characteristic of the transducer 130, the above process may be clearly understood to those skilled in the art.

Each respective one of the first reflected signal, the second reflected signal, and the like which are received by the ultrasonic image generating apparatus 100 may be stored in association with corresponding focal positions.

Stored signals, such as those described above, may be used to generate an ultrasonic image with respect to the target field of view.

When the transducer 130 receives a first reflected signal which relates to the first ultrasonic pulse and a second reflected signal which relates to the second ultrasonic signal, a corresponding focal position may be adjusted based on the target field of view.

As illustrated in FIG. 2, a plurality of pulses which have respective frequency bands f1, f2, . . . fN are transmitted to corresponding depth positions z1, z2, . . . zN, and then the pulses are focused and are simultaneously transmitted.

When respective reflected signals are received with respect to the respective depths, separation may be performed by using the orthogonality of the signals, and an ultrasonic image may be generated by using the resulting separated signals.

According to an exemplary embodiment, there may be provided a method for generating an ultrasonic image, the method including generating a first ultrasonic pulse which has a first center frequency and a first bandwidth and a second ultrasonic pulse which has a second center frequency and a second bandwidth, transmitting the first ultrasonic pulse and the second ultrasonic pulse by using an ultrasonic transducer which has an ultra-wideband transfer characteristic, and receiving a first reflected signal which corresponds to the first ultrasonic pulse and a second reflected signal which corresponds to the second ultrasonic pulse and using the first and second reflected signals to generate an ultrasonic image.

The ultrasonic image generating method is described above with reference to FIG. 1 and FIG. 2.

The ultrasonic image generating method may further include controlling the ultrasonic transducer to increase the number of ultrasonic focal points when an instruction which relates to increasing a lateral resolution of an ultrasonic image to be generated is received.

Further, the ultrasonic image generating method may further include controlling the ultrasonic transducer to decrease the number of ultrasonic focal points when an instruction which relates to increasing an axial resolution of an ultrasonic image to be generated is received.

Figure 3:
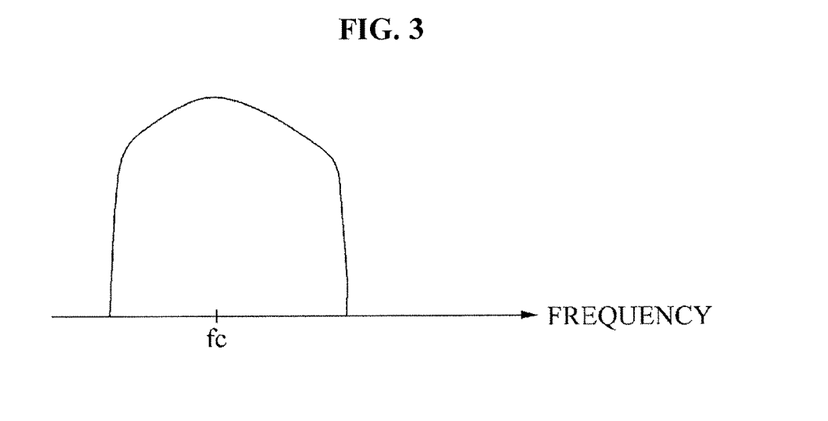
FIG. 3 and FIG. 4 are graphs which illustrate an example of a frequency response of an ultra-wideband transducer by using a comparison with a conventional transducer, according to an exemplary embodiment.
Figure 4:
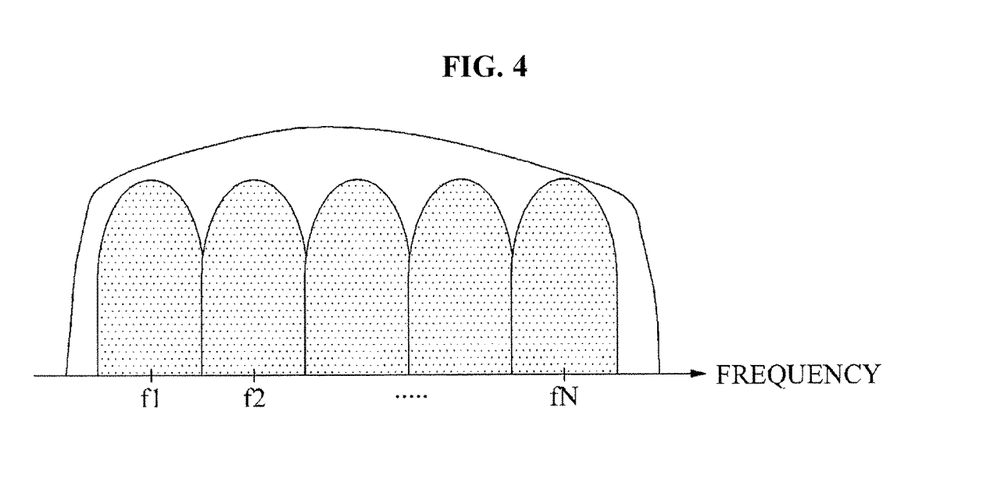

FIG. 3 and FIG. 4 show graphs which illustrate an example of a frequency response of an ultra-wideband transducer by using a comparison with a conventional transducer.

Referring to a frequency response of an existing ultrasonic transducer as illustrated in FIG. 3, a unit transducer has a single frequency response characteristic and transmits an ultrasonic wave.

An ultra-wideband ultrasonic transducer, as illustrated in FIG. 4 according to an exemplary embodiment, may divide a frequency band into a plurality of subbands to be used for respective pulses based on a predetermined purpose and a field of view.

Accordingly, due to the use of a ultra-wideband transducer, dynamic transmission focusing may be performed by dividing a frequency band into at least two frequency bands and by focusing a high frequency pulse with respect to a portion which is relatively close to a transducer transmitter, that is, a relatively shallow portion of a diagnosis target, and by focusing a low frequency pulse with respect to a portion which is relatively far away from the transducer transmitter, that is, a relatively deep portion of the diagnosis target. However, according to another exemplary embodiment, it is possible to focus a high frequency pulse with respect to a deep portion of the diagnosis target and to focus a low frequency pulse with respect to a shallow portion based on a user convenience or necessity.

A user may select the number of focal zones or focal points based on user purposes or a field of view. In this example, based on an increase in the number of focal points, a frequency band of a pulse may decrease and an axial resolution may be degraded, and the number of transmission focal positions may increase. Accordingly, a lateral resolution may be enhanced.

Accordingly, by using an ultrasonic transducer which has a wideband frequency band or an ultra-wideband frequency band, each frequency divided signal may be designed to have a frequency band of an ultrasonic pulse which may otherwise be transmitted by using an existing ultrasonic transducer.

Figure 7:
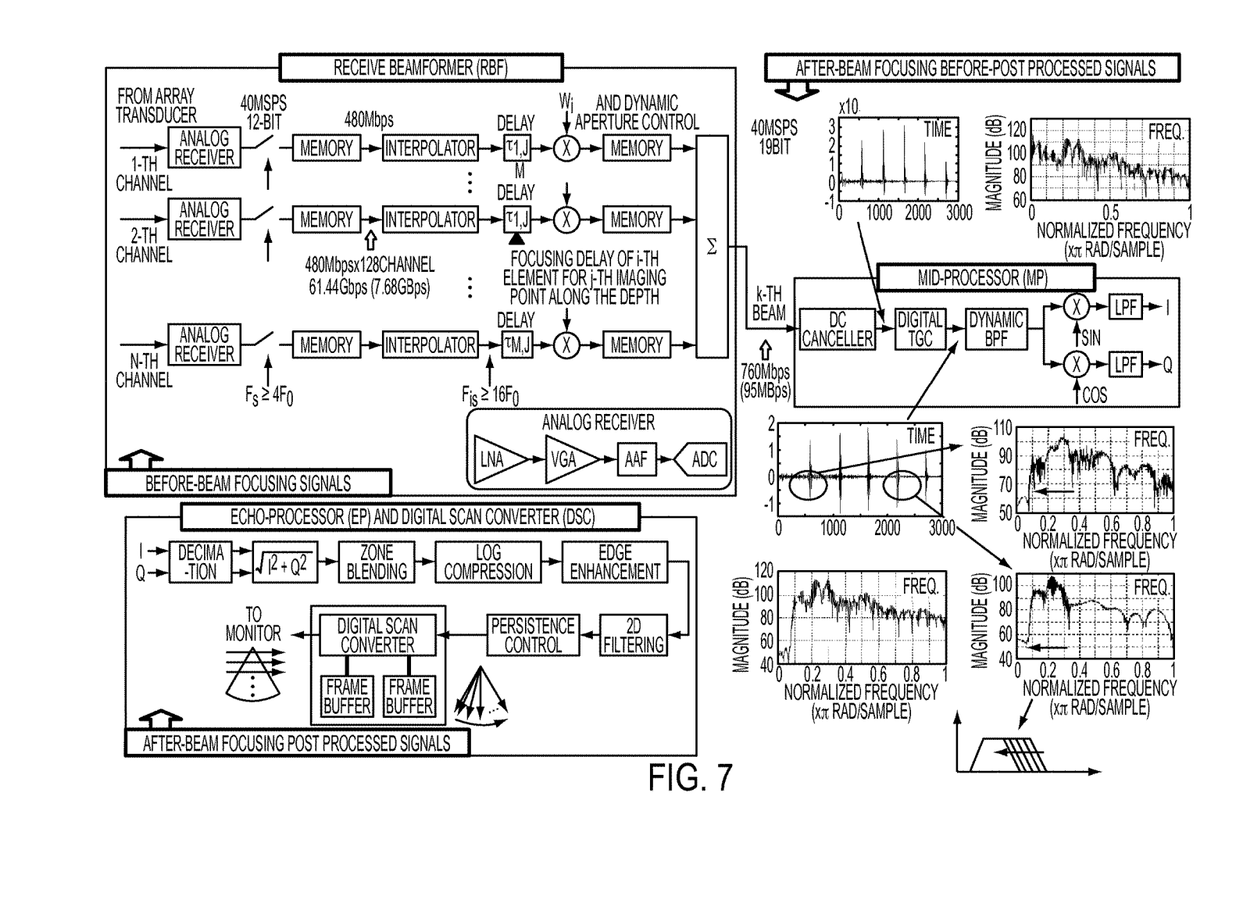
FIG. 7 is a diagram which illustrates processes for generating ultrasonic images relating to before-beam focusing signals, after-beam focusing before-post processing signals, and after-beam focusing post processed signals, according to an exemplary embodiment.

Referring to FIG. 7, in an exemplary embodiment, an ultrasonic image generating apparatus may be used to display an image, such as, for example, a medical image, which image is a result of using signals which are processed according to methods described above. For example, a primary medical image may be generated by using before-beam focusing signals which are processed by a received beamformer, as illustrated at a top left-side portion of FIG. 7. Alternatively, a secondary medical image may be generated by using after-beam focusing before-post processed signals which are processed by a mid-processor, as illustrated at a right-side portion of FIG. 7. As another alternative, a tertiary medical image may be generated by using after-beam focusing post processed signals which are processed by an echo-processor and/or a digital scan converter, as illustrated at a bottom left-side portion of FIG. 7.

In yet another exemplary embodiment, an ultrasonic medical imaging system is provided. The ultrasonic medical imaging system comprises a handholdable probe, a processor which is connected to the probe, and a display which displays an image relating to a target human body portion which is a subject of a medical diagnosis. The handholdable probe includes a single ultrasonic transducer which has a frequency transfer characteristic for which a 6-dB bandwidth is greater than 100% of a center frequency of a frequency band of the transducer. The transducer includes a curved contact portion via which ultrasonic pulses are emitted toward the target human body portion and via which reflected signals are received. The processor uses the received reflected signals to generate the displayed image.

In the frequency transfer characteristic, the 6-dB bandwidth may be greater than 120% and less than 180% of the center frequency of the frequency band of the transducer. The single ultrasonic transducer may include one of a capacitive micromachined ultrasonic transducer (cMUT) and a piezoelectric micromachined ultrasonic transducer (pMUT).

The processor may be configured to perform at least one beam focusing operation with respect to the received reflected signals, and to generate a first image based on a result of the at least one beam focusing operation. The processor may be further configured to perform at least one coherent summing operation with respect to the result of the at least one beam forming operation, and to generate a second image based on a result of the at least one coherent summing operation. The processor may be further configured to perform at least one digital scan conversion operation with respect to the result of the at least one coherent summing operation, and to generate a third image based on a result of the at least one digital scan conversion operation.

The processes, functions, methods and/or software described above may be recorded, stored, or fixed in one or more non-transitory computer-readable storage media that includes program instructions to be implemented by a computer to cause a processor to execute or perform the program instructions. The media may also include, alone or in combination with the program instructions, data files, data structures, and the like. The media and program instructions may be specially designed and constructed, or they may be of a kind which is well-known and available to those having skill in the computer software arts. Examples of non-transitory computer-readable media include magnetic media such as hard disks, floppy disks, and magnetic tape; optical media such as compact-disk read-only memory (CD ROM) disks and digital versatile disks (DVDs); magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer while using an interpreter. The described hardware devices may be configured to act as one or more software modules in order to perform the operations and methods described above, or vice versa. In addition, a non-transitory computer-readable storage medium may be distributed among computer systems which are connected via a network, and non-transitory computer-readable codes or program instructions may be stored and executed in a decentralized manner.

According to exemplary embodiments, there may be provided an ultrasonic image generating apparatus and method that may simultaneously enhance a frame rate and a resolution of an ultrasonic image.

According to exemplary embodiments, there may be provided an ultrasonic image generating apparatus and method that may enhance diagnostic accuracy to be suitable for the medical ultrasonic image field and that also may enable various parameters of an ultrasonic transducer to be user selectable based on user convenience or medical purposes.

A number of exemplary embodiments have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for generating an ultrasonic image, comprising:
   an ultrasonic transducer which has an ultra-wideband frequency transfer characteristic;
   a pulse generator which generates a plurality of ultrasonic pulses, wherein each pulse of the plurality of ultrasonic pulses has a different respective center frequency within a frequency band of the ultrasonic transducer, wherein the pulse generator comprises a plurality of bandpass filters;
   a controller which controls the pulse generator to:
      generate a first ultrasonic pulse using a first bandpass filter of the plurality of bandpass filters, wherein the first ultrasonic pulse corresponds to a first focal point at a first depth,
      generate a second ultrasonic pulse using a second bandpass filter of the plurality of bandpass filters, wherein the second ultrasonic pulse corresponds to a second focal point at a second depth different than the first depth, and the second ultrasonic pulse is orthogonal to the first ultrasonic pulse;
   an ultrasonic transducer configured to simultaneously transmit the first ultrasonic pulse and the second ultrasonic pulse; and
   a processor configured to generate, based on reflected signals corresponding to the first ultrasonic pulse and the second ultrasonic pulse, the ultrasonic image.

2. The apparatus of claim 1, wherein, in the ultra-wideband frequency transfer characteristic, a −6 dB bandwidth is greater than 120% of the center frequency of the frequency band of the ultrasonic transducer.

3. The apparatus of claim 1, wherein the ultrasonic transducer comprises one of a capacitive micromachined ultrasonic transducer (cMUT) and a piezoelectric micromachined ultrasonic transducer (pMUT).

4. The apparatus of claim 1, wherein sample signals received via the ultrasonic transducer are wirelessly transmitted to a target which is positioned outside of the apparatus.

5. An apparatus for generating an ultrasonic image, the apparatus comprising:
   a pulse generator which generates a first ultrasonic pulse which has a first center frequency and a first bandwidth and a second ultrasonic pulse which has a second center frequency and a second bandwidth, wherein the pulse generator comprises a plurality of bandpass filters;
   a transducer which has an ultra-wideband frequency transfer characteristic and which simultaneously transmits the first ultrasonic pulse and the second ultrasonic pulse;
   a controller which controls the pulse generator to:
      generate a first ultrasonic pulse using a first bandpass filter of the plurality of bandpass filters, wherein the first ultrasonic pulse corresponds to a first focal point at a first depth,
      generate a second ultrasonic pulse using a second bandpass filter of the plurality of bandpass filters, wherein the second ultrasonic pulse corresponds to a second focal point at a second depth different than the first depth, and the second ultrasonic pulse is orthogonal to the first ultrasonic pulse;
   an ultrasonic transducer configured to simultaneously transmit the first ultrasonic pulse and the second ultrasonic pulse; and a processor configured to generate, based on reflected signals corresponding to the first ultrasonic pulse and the second ultrasonic pulse, the ultrasonic image.

6. The apparatus of claim 5, wherein when the transducer receives a first reflected signal which relates to the first ultrasonic pulse and a second reflected signal which relates to the second ultrasonic pulse, storage is performed in a memory of the apparatus by performing radio frequency (RF)-echo signal sampling with respect to each of the first reflected signal and the second reflected signal, and dynamic focusing is performed with respect to each of the first reflected signal and the second reflected signal.

7. The apparatus of claim 5, wherein the first bandpass filter is configured by using at least one of a matched filter, a correlator, an inverse filter, and a signal processor.

8. The apparatus of claim 5, wherein each of a first separated reflection signal and a second separated reflection signal is stored in a memory in association with a corresponding focal position, and an ultrasonic image which relates to a target field of view is generated by using the stored signals.

9. The apparatus of claim 8, wherein the target field of view is received from a user via a user interface, and at least one of the first center frequency, the first bandwidth, the second center frequency, and the second bandwidth is adjusted based on the target field of view.

10. The apparatus of claim 8, wherein when the transducer receives at least one of the first reflected signal and the second reflected signal, a corresponding focal position of the at least one received signal is adjusted based on the target field of view.

11. The apparatus of claim 1, wherein the ultrasonic transducer simultaneously transmits at least two ultrasonic pulses from among the plurality of ultrasonic pulses.

* * * * *